United States Patent
Drenten et al.

(10) Patent No.: US 7,218,449 B2
(45) Date of Patent: May 15, 2007

(54) OPTICAL DEVICE FOR SCANNING AN OPTICAL RECORD CARRIER

(75) Inventors: Ronald Reindert Drenten, Eindhoven (NL); Peter Coops, Eindhoven (NL); Petrus Theodorus Jutte, Eindhoven (NL)

(73) Assignee: Koninklijke Philips Electronics N. V., Eindhoven (NL)

( * ) Notice: Subject to any disclaimer, the term of this patent is extended or adjusted under 35 U.S.C. 154(b) by 69 days.

(21) Appl. No.: 10/498,950

(22) PCT Filed: Dec. 10, 2002

(86) PCT No.: PCT/IB02/05373

§ 371 (c)(1), (2), (4) Date: Jun. 16, 2004

(87) PCT Pub. No.: WO03/054865

PCT Pub. Date: Jul. 3, 2003

(65) Prior Publication Data

US 2005/0078373 A1 Apr. 14, 2005

(30) Foreign Application Priority Data

Dec. 21, 2001 (EP) ................................. 01205129

(51) Int. Cl.
*G02B 5/18* (2006.01)
*G11B 7/00* (2006.01)

(52) U.S. Cl. ...................... 359/569; 359/571; 359/572; 369/112.05; 369/112.03

(58) Field of Classification Search ................ 359/569, 359/571, 574, 572, 573; 369/112.01, 112.12, 369/112.03, 112.05, 112.07
See application file for complete search history.

(56) References Cited

U.S. PATENT DOCUMENTS 4,338,012 A * 7/1982 Matsumura et al. ......... 396/150
2001/0021163 A1 * 9/2001 Yukawa .................. 369/112.12

* cited by examiner

*Primary Examiner*—Audrey Chang

(57) ABSTRACT

An optical device for scanning an optical record carrier (20) has a radiation source (25) that can emit two radiation beams of different wavelength along different optical paths (28, 29). The emitted radiation is focused on the record carrier and reflected back to a detection system (40). A beam combiner 43 is arranged in the optical path between the radiation source and the detection system for combining the two radiation beams on one optical path, thereby allowing the use of a single detection system for both radiation beams. The beam combiner includes a grating that passes one of the beams undiffracted and diffracts the other beam mainly in the first order. The profile of the grating lines show alternating slanting grooves and slanting lands.

7 Claims, 4 Drawing Sheets

OPTICAL DEVICE FOR SCANNING AN OPTICAL RECORD CARRIER

BACKGROUND OF THE INVENTION

1. Field of the Invention

The invention relates to an optical device for scanning an optical record carrier, and to an optical grating for use in such a device. More particularly, the device includes a radiation source for generating a first radiation beam of a first wavelength traveling along a first path and a second radiation beam of a different, second wavelength traveling along a different, second path, a photo-detection system, an optical system for guiding the radiation beams via the optical record carrier to the photo-detection system, and a grating for combining the first and second beams such that they substantially coincide on the photo-detection system. Scanning may refer to reading, writing and erasing information from the record carrier.

2. Description of the Related Art

The increasing demand for storage capacity has led to the development of new optical scanning devices and matching record carriers having an increased storage capacity. As a consequence, old, low capacity record carriers and new, high capacity record carriers are simultaneously available on the market. For compatibility reasons, a scanning device for a new record carrier should be able to scan both old and new record carriers. This requires adaptation of the device to handle the different formats of the record carriers. As an example, a scanning device designed for scanning both the newer record carrier of the DVD type and the older writable record carrier of the CD-R type must form a 650 nm wavelength radiation beam for scanning the DVD and a 780 nm wavelength radiation beam for scanning the CD. The optical system of such a player includes two diode lasers, one for 650 nm radiation and one for 780 nm radiation. To reduce the cost of the optical system, as many of its components as possible should be traversed by both radiation beams.

Such a dual wavelength scanning device is known from U.S. Pat. No. 5,912,868 and is schematically presented in FIG. 1. Paths 1 and 2 of the two radiation beams from lasers 3 and 4 are mutually oriented under 90° and combined in a cube beam splitter 5 before entering an objective system 6 that focuses the beams on a record carrier 7. The choice of which radiation source is operated is determined by the type of record carrier being scanned. Radiation returning from the record carrier is guided to a photo-detection system 8 via a beam splitter 9. The photo-detector transforms the impinging radiation into electrical signals that represent information stored on the record carrier and tracking information indicating the positional accuracy of the focus of the radiation beam on the tracks of the record carrier on which the information is written. The tracking relates to tracking in a direction of the optical axis, i.e., focusing, and the tracking in a direction perpendicular to both the optical axis and the direction of a track being scanned in the record carrier. The latter type of tracking is also referred to as radial tracking where it relates to disc-shaped optical record carriers.

The tolerance in the mutual position of the two lasers is relatively tight in view of the accuracy with which the radiation beams must fall on the detection system. Errors in the position on the detection system may cause errors in the tracking information. FIG. 2 shows a scanning device known from Japanese Patent Application No. JP-A 10326428, in which the two lasers are arranged close together, drawn as a single component 10, making it easier to keep their mutual position within the tolerance. The paths of the two radiation beams are at an acute angle, and the beams are combined by a grating 11. The grating diffracts both incident radiation beams in transmission. The $zero^{th}$-order beam of one of the radiation beams passes from the grating to the objective system, whereas the first-order beam of the other radiation beam passes along the same path to the objective system.

Japanese Patent Application No. JP-A 10261241 discloses a grating for combining the radiation beams from the lasers. The grating is optimized for transmission of the radiation of 650 nm wavelength in the $zero^{th}$ order and radiation of 780 nm in the first order. The ruling of the grating is in the form of a series of adjacent saw-tooth profiles, each saw-tooth being approximated by a stepped profile.

SUMMARY OF THE INVENTION

Since a high transmittance of the grating is desirable for reading of and, in particular, writing information in the record carrier at a high data rate, it is an object of the invention to provide a dual wavelength scanning device having a grating as beam combiner which has a higher transmittance. It is also an object to reduce the complexity of the ruling of the grating to facilitate its manufacture.

This object is achieved if, according to the invention, the scanning device is provided with a grating having alternating slanting grooves and slanting lands. The transmittance can be made more than 80% for both the $zero^{th}$ order beam of the first wavelength beam and the first order beam of the second wavelength beam. The reduced complexity of the ruling simplifies the manufacture of the grating. Since the ruling has fewer edges than the known grating, it can be made more accurately. The improved accuracy reduces the amount of stray light caused by the grating, and, hence, increases the transmittance of the grating.

The transmitted power of the grating in the $zero^{th}$ order beam is increased, when the grooves have an optical depth substantially equal to an integer number times the first wavelength and, at the same time, an odd integer number times half of the second wavelength. The term "substantially equal" means equal to within +/−0.2 wavelengths.

If the grating is a transmission grating provided in a plane, the grooves and lands slant preferably with respect to the plane at an angle approximately equal to the angle between an undiffracted beam and a selected diffracted beam from the second radiation beam. The term "approximately equal" means equal to within +/−50%, preferably within 15%. The slant of the grooves and lands increases the transmittance of the first-order beam diffracted from the second-wavelength beam.

If the grating is a reflection grating provided in a plane, the grooves and lands slant preferably with respect to the plane at an angle approximately equal to ¼ times the angle between an undiffracted beam and a selected diffracted beam from the second radiation beam.

The alignment of the radiation beams coming from the record carrier and incident on the detection system may be facilitated by arranging the radiation source and the grating mutually adjustable. In addition, the grating and the photo-detection system can be made mutually adjustable. The two degrees of freedom required for proper alignment are a rotation of the grating around the optical axis and a change of the position of the grating along the optical axis.

When the grating is arranged immediately behind the radiation source, both beams follow the same path from the grating to the photo-detection system. Alternatively, when the grating is arranged in front of the photo-detection system, the beams form spots at the same location on the photo-sensitive area of the photo-detection system; between the radiation source and the grating the beams follow different optical paths, albeit substantially parallel.

In another aspect of the invention, an optical grating for unifying paths of a first radiation beam of a first wavelength incident along a first path and a second radiation beam of a different, second wavelength incident along a different, second path such that an undiffracted beam from the first radiation beam and a diffracted beam from the second radiation beam substantially coincide, is characterized in that the grating has alternating slanting grooves and slanting lands. Preferably, the grooves have an optical depth substantially equal to an integer number times the first wavelength. More preferably, the grooves have, at the same time, an optical depth substantially equal to an odd integer number times half the second wavelength. This condition optimizes the diffraction efficiency for both wavelengths in the desired direction.

BRIEF DESCRIPTION OF THE DRAWINGS

Features and advantages of the invention will become apparent from the following description, given by way of example only, of preferred embodiments of the invention, which refers to the accompanying drawings, wherein.

DESCRIPTION OF THE PREFERRED EMBODIMENTS

Figure 1:
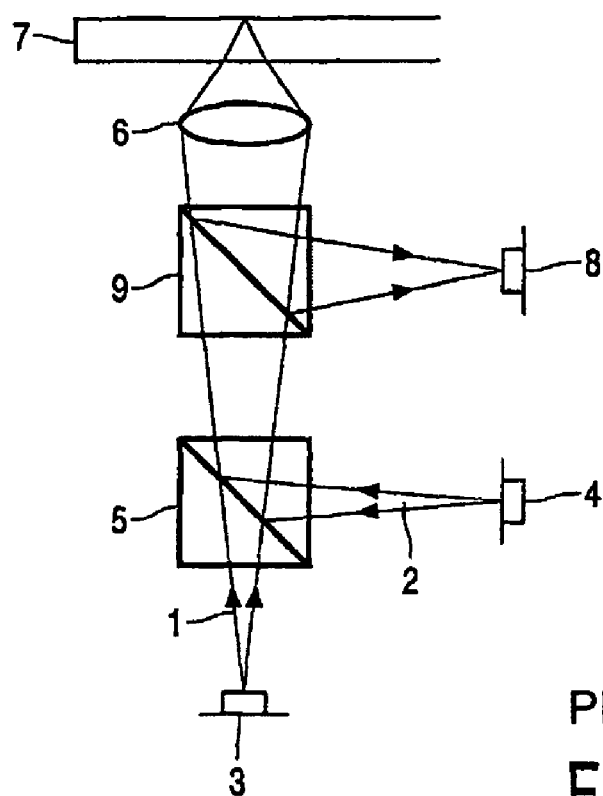
FIGS. 1 and 2 show schematically prior art scanning devices.
Figure 2:
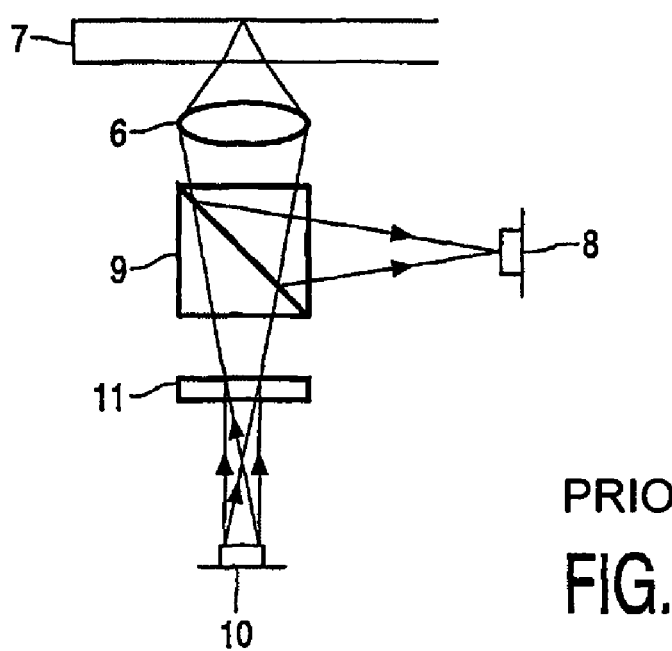
Figure 3:
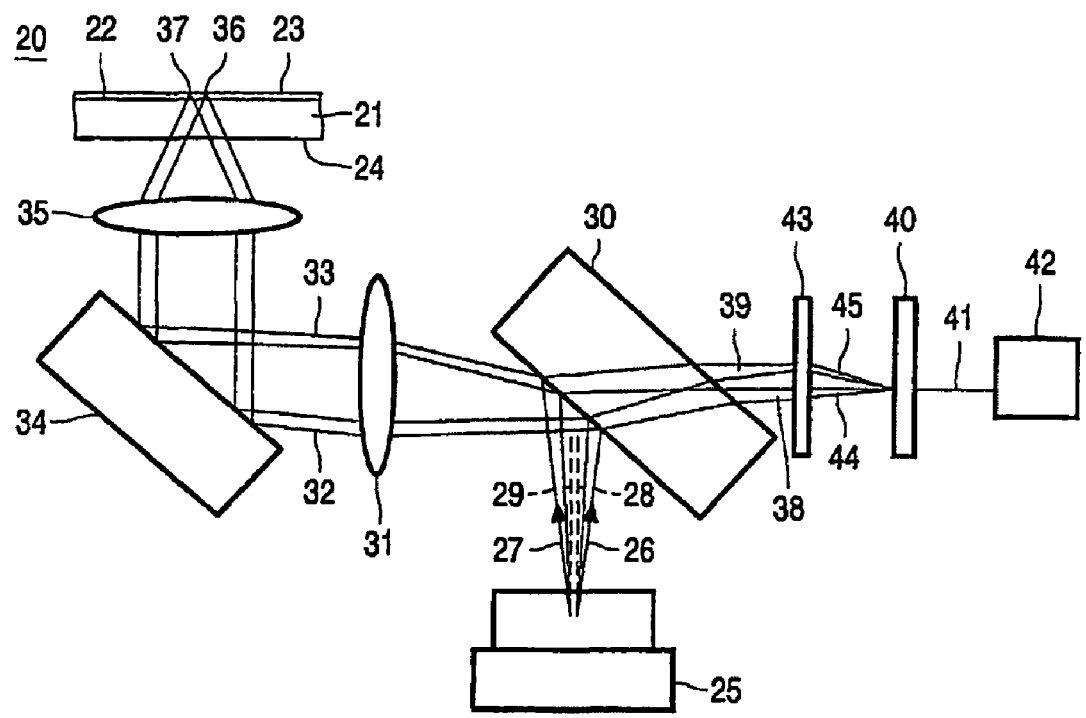
FIG. 3 shows a scanning device according to the invention.

FIG. 3 shows a scanning device according to the invention for scanning an optical record carrier 20. The record carrier comprises a transparent layer 21, on one side of which an information layer 22 is arranged. The side of the information layer facing away from the transparent layer is protected from environmental influences by a protection layer 23. The side of the transparent layer facing the device is called the entrance face 24. The transparent layer 21 acts as a substrate for the record carrier by providing mechanical support for the information layer. Alternatively, the transparent layer may have the sole function of protecting the information layer, while the mechanical support is provided by a layer on the other side of the information layer, for instance, by the protection layer 23 or by a further information layer and a transparent layer connected to the information layer 22. Information may be stored in the information layer 22 of the record carrier in the form of optically detectable marks arranged in substantially parallel, concentric or spiral tracks, not indicated in the Figure. The marks may be in any optically readable form, e.g., in the form of pits, or areas with a reflection coefficient or a direction of magnetization different from their surroundings, or a combination of these forms.

The scanning device comprises a radiation source 25 that can emit a first radiation beam 26 having a first wavelength and a second radiation beam 27 having a second wavelength. The dashed lines 28 and 29 indicate the principal rays of the radiation beams 26 and 27, respectively. Although these radiation beams travel through the same optical elements 30, 31, 34, 35, 43 from the radiation source to the detection system, they are said to follow different paths because their principal rays do not coincide. The radiation beam 26 follows a first path and the radiation beam 27 follows a second path through the optical elements.

The radiation source may include a first and a second semiconductor laser emitting at nominal wavelengths of 650 and 780 nm, respectively. The first laser will be operated when the record carrier being scanned is of the DVD type and the second laser will be operated when the record carrier is of the CD type. The two lasers may be integrated on one semiconductor chip, allowing a distance of the emission points of the lasers of the order of 100 μm.

A beam splitter 30 reflects the diverging radiation beams 26 and 27 towards a collimator lens 31, which converts the diverging beams 26 and 27 into collimated beams 32 and 33. After reflection on a mirror 34, the collimated beams are incident on an objective system 35. The objective system may include one or more lenses and/or a grating. The objective system 35 changes the beams 32 and 33 to converging beams, incident on the entrance face 24 of the record carrier 20. The objective system has a spherical aberration correction adapted for passage of the radiation beam through the thickness of the transparent layer 21. The converging beams form spots 36 and 37 on the information layer 22. Radiation reflected by the information layer 22 forms diverging beams, transformed into substantially collimated beams by the objective system 35 and subsequently into converging beams 38 and 39 by the collimator lens 31. The beam splitter 30 separates the forward and reflected beams by transmitting at least part of the converging beams from the record carrier towards a detection system 40. The detection system captures the radiation and converts it into electrical output signals 41.

A signal processor 42 converts these output signals to various other signals. One of the signals is an information signal, the value of which represents information read from the information layer 22. The information signal is processed by an information processing unit for error correction. The signal processor 42 also provides other signals, such as the focus error signal and a radial error signal. The focus error signal represents the axial difference in height between the spot 36 or 37 and the information layer 22. The radial error signal represents the distance in the plane of the information layer 22 between the spot 36 or 37 and the center of a track in the information layer to be followed by the spot. The focus error signal and the radial error signal are fed into a servo circuit for controlling a focus actuator and a radial actuator, respectively. The actuators are not shown in the Figure. The focus actuator controls the position of the objective system 35 in the focus direction, thereby controlling the actual position of the spot 36 or 37 such that it coincides substantially with the plane of the information layer 22. The radial actuator controls the position of the objective lens 35 in a radial direction, thereby controlling the radial position of the spot 36 or 37 such that it coincides substantially with the central line of track to be followed in the information layer 22. The tracks in the Figure run in a direction perpendicular to the plane of the Figure.

A beam combiner 43 in the form of a grating, arranged in the optical paths of the beams before the detection system 40, forms an undiffracted beam 44 from the beam 38 and a first-order diffracted beam 45 from the beam 39. The beams 44 and 45 converge at substantially the same location on the photo-sensitive surface of the detection system 40. Hence, only a single detection system and accompanying electronics is required for the two different radiation beams.

Although the scanning device shown in FIG. 3 uses the first-order beam 45 diffracted from the beam 39 and the undiffracted beam 44 from the beam 38, other combinations of diffracted orders are possible, e.g., a first-order beam from both beams 38 and 39. The use of an undiffracted beam has advantages in devices that can write information on the record carrier. When a semi-conductor laser is used as radiation source, the wavelength of the radiation shows a small shift, of the order of a few nanometers, when changing the radiation power from the read level to the higher write level. If such a radiation beam is diffracted in the first order by a grating such as the beam combiner 43, a change in the diffraction angle will occur, resulting in a change in the position of the spot on the record carrier and/or the detection system. Therefore, the beam that is switched in power between the read and write level is preferably transmitted or reflected undiffracted by the beam combiner grating. Hence, in a scanning device that is able to read and write in the CD format and read only in the DVD format, the 785 nm beam for CD should be undiffracted and the 650 nm beam for DVD should be diffracted, preferably in the first order.

Figure 4:
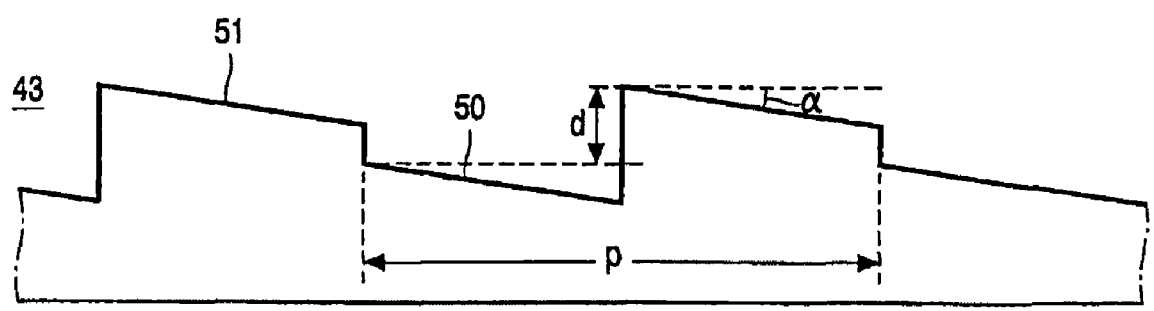
FIG. 4 shows the profile of a beam combining grating according to the invention.

FIG. 4 shows a cross-section through the profile of an embodiment of the grating 43 according to the invention in a direction perpendicular to the grating lines. A grating line has a crenellated profile of a groove 50 and a land 51. The flat bottom of the groove and the flat land slant at an angle $\alpha$ with respect to the plane of the beam combiner 43 in which the grating is arranged. The angle $\alpha$ is chosen to make the intensities of the diffracted beam and the non-diffracted beam equal. For a transmission grating, the angle $\alpha$ is chosen substantially equal to the angle $\theta$, the angle between the diffracted beam and the undiffracted beam. The sine of the angle $\theta$ for a first-order beam diffracted in transmission is equal to $\lambda/(2(n-1)p)$, where $\lambda$ is the wavelength of the beam, n the refractive index of the material of the grating and p the pitch of the grating. This reduces to $\sin\theta \approx \lambda/p$ for most glasses and plastics, which have $n \approx 1.5$. The grating lines have a pitch "p" and a depth "d" as indicated in the Figure. The transmission of the grating for the undiffracted beam 43 is optimized by choosing the depth "d" such that it corresponds to a phase depth equal to a multiple of $2\pi$ for the wavelength of the radiation beam 38. The phase depth for the air-incident transmission grating is substantially equal to $2\pi d(n-1)/\lambda$, where n is the refractive index of the grating material and $\lambda$ is the wavelength of the incident radiation.

Figure 6:
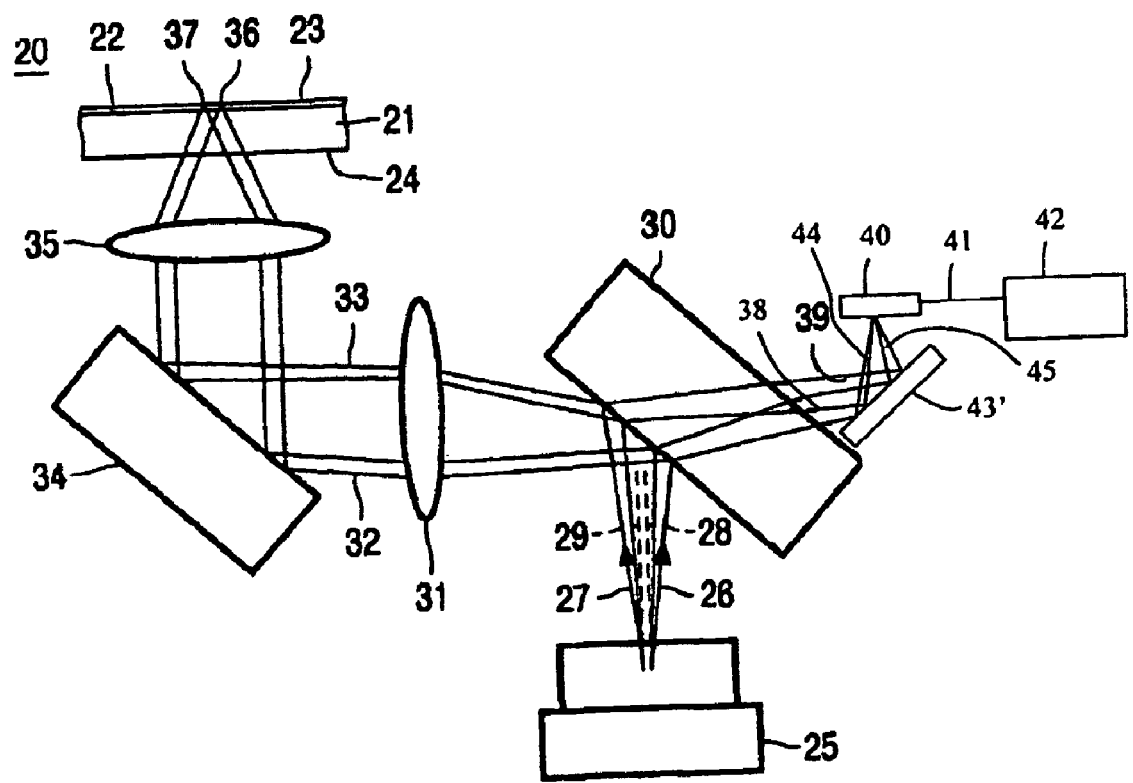
FIG. 6 shows a scanning device as in FIG. 3 with a reflective grating.

Instead of a transmission grating, a reflection grating may be used in the device. This is shown in FIG. 6 in which a scanning device substantially the same as that shown in FIG. 3 uses a reflection grating 43'. An air-incident reflection grating has a phase depth substantially equal to $4\pi d/\lambda$. In that case, the angle $\alpha$ should be chosen substantially equal to $\theta/4$, which is equal to $1/(4p)$ for a first-order diffracted beam.

In a particular embodiment of the scanning device, the parameters have the following values: the first wavelength, i.e., that of the radiation beam 38, is 650 nm, the second wavelength, i.e., that of the radiation beam 39, is 785 nm, the refractive index of the grating material is 1.5, the diffraction angle $\theta$ for the second wavelength is 1.7° and a separation between the spots of the radiation beams 44 and 45 on the detection system 40 without grating 43 equal to 120 µm. The pitch "p", equal to $\lambda 2/\sin\theta$, is now 26.5 µm. The phase depth of the grating for the first wavelength is taken to be equal to $6\pi$, corresponding to a depth "d" equal to 3.9 µm. The phase depth of the grating for the second wavelength is $4.95\pi$. Since this corresponds to approximately anti-phase, the radiation beam of the second wavelength will form a low-intensity undiffracted beam and a high-intensity diffracted beam.

Figure 5:
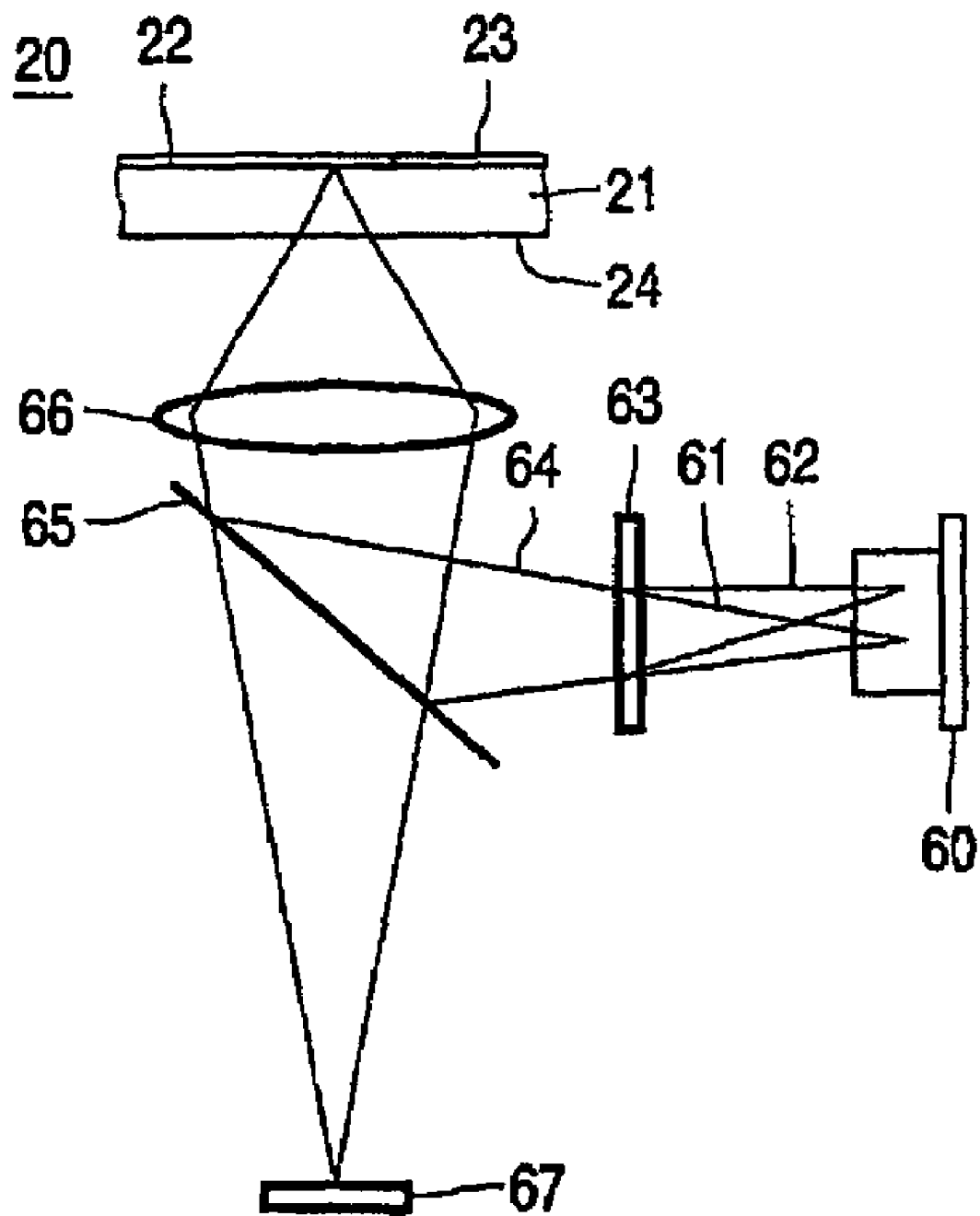
FIG. 5 shows a further embodiment of the scanning device.

FIG. 5 shows a further embodiment of the scanning device according to the invention, in which the beams are combined close to the radiation source instead of close to the detection system as shown in FIG. 3. A radiation source 60 can emit two radiation beams 61 and 62 of different wavelength. Both beams are incident on a beam combiner 63 according to the invention. The beam combiner includes a grating having a profile as shown in FIG. 4. A beam 64 coming from the beam combiner is the undiffracted beam from the incident beam 61 and/or the first-order diffracted beam from the incident beam 62. The beam 64 is focused on the information layer 22 of the record carrier 20 via a beam splitter 65 and an objective system 66. Radiation reflected by the record carrier is transmitted by the beam splitter 65 and intercepted by a detection system 67. The optical system of the scanning device shown in FIG. 5 is advantageous compared to that shown in FIG. 3, because the former has a single optical path through the objective lens for the radiation beams of different wavelength, thereby reducing the use of the field of the objective lens.

The optical grating according to the invention may advantageously be used in an optical scanning device as described in the European Patent Application No. EP01/10737, corresponding to U.S. Patent Application Publication No. 2002/0051247. This device uses a beam combiner having two gratings, one on each side of a plate. One or both gratings may have slanting grooves and slanting lands.

The invention claimed is:

1. An optical device for scanning an optical record carrier, said optical device comprising:
   a radiation source for generating a first radiation beam of a first wavelength traveling along a first path and a second radiation beam of a different, second wavelength traveling along a different, second path;
   a photo-detection system;
   an optical system for guiding the radiation beams via the optical record carrier to the photo-detection system; and
   a grating for combining the first and second beams such that they substantially coincide on the photo-detection system, characterized in that the grating has alternating slanting grooves and slanting lands, thereby enabling said grating to have a high transmittance for a zero$^{th}$ order beam of the first radiation beam of the first wavelength and for a first order beam of the second radiation beam of the second wavelength.

2. The optical device as claimed in claim 1, wherein the grooves have an optical depth equal to substantially an integer number times the first wavelength and, at the same time, substantially an odd integer number times half of the second wavelength.

3. The optical device as claimed in claim 1, wherein the grating is a transmission grating provided in a plane and the grooves and lands slant with respect to the plane at an angle approximately equal to the angle between an undiffracted beam from the first radiation beam and a selected diffracted beam from the second radiation beam.

4. The optical device as claimed in claim 1, wherein the grating and the radiation source are mutually adjustably positioned.

5. The optical device as claimed in claim 4, wherein the grating and the photo-detection system are mutually adjustably positioned.

6. The optical device as claimed in claim 1, wherein the grating and the photo-detection system are mutually adjustably positioned.

7. An optical device for scanning an optical record carrier, said optical device comprising:
- a radiation source for generating a first radiation beam of a first wavelength traveling along a first path and a second radiation beam of a different, second wavelength traveling along a different, second path;
- a photo-detection system;
- an optical system for guiding the radiation beams via the optical record carrier to the photo-detection system; and
- a grating for combining the first and second beams such that they substantially coincide on the photo-detection system, characterized in that the grating is a reflection grating provided in a plane has alternating slanting grooves and slanting lands, thereby enabling said grating to have a high reflectance for a zero$^{th}$ order beam of the first radiation beam of the first wavelength and for a first order beam of the second radiation beam of the second wavelength, wherein the grooves and lands slant with respect to the plane at an angle approximately equal to ¼ times the angle between an undiffracted beam from the first radiation beam and a selected diffracted beam from the second radiation beam.

* * * * *